US006147350A

United States Patent [19]
Beecroft et al.

[11] Patent Number: 6,147,350
[45] Date of Patent: Nov. 14, 2000

[54] SPECTROSCOPIC RESIDUE DETECTION SYSTEM AND METHOD

[75] Inventors: Michael Beecroft, Temecula, Calif.; Marian Martin Szczesniak, Winston-Salem, N.C.

[73] Assignee: Surface Optics Corporation, San Diego, Calif.

[21] Appl. No.: 09/221,771

[22] Filed: Dec. 28, 1998

[51] Int. Cl.[7] ....................................................... G01J 5/02
[52] U.S. Cl. ....................................................... 250/339.08
[58] Field of Search ............................. 250/228, 339.08; 356/236, 346, 445–448, 244, 73, 246

[56] References Cited

U.S. PATENT DOCUMENTS 4,583,860  4/1986  Butner .
5,258,363  11/1993  Hed .

OTHER PUBLICATIONS

Eckerle "Averaging ... Design"; Applied Optics vol. 15, No. 3 pp. 703–707 356/236, Mar. 1976.

*Primary Examiner*—K. P. Hantis
*Attorney, Agent, or Firm*—John R. Ross; John R. Ross, III

[57] ABSTRACT

A spectroscopic detection system and method for quantitative measurements of non-volatile residues. A sample to be analyzed is spread out on the inside surface of a cup portion of a unique detector cup. The cup portion mates with a detector portion to create an enclosed reflecting volume. A small port in the detector portion permits entrance of light which diffusely reflects multiple times from the inside surface of the enclosed reflecting volume and which is partially absorbed by the sample depending on the spectral absorption characteristics of the sample. A light detector in the detector portion detects light after multiple reflections from the surfaces of the detector and cup portions and multiple passes through the sample on the surface of the cup portion. Light detected by the light detector is spectrally analyzed to determine the spectral characteristics of the sample. In a preferred embodiment of the present invention the light is infrared light, the diffusely reflecting volume is a sphere, the reflecting surface of the cup is a smooth hemispheric gold surface and the reflecting surface of the detector portion is a rough hemispheric gold surface. In this preferred embodiment light from a broad band infrared light source is directed through an interferometer system prior to entering the detector cup and signals from the light detector are Fourier analyzed along with mirror position data to determine absorption characteristics of the sample.

27 Claims, 6 Drawing Sheets

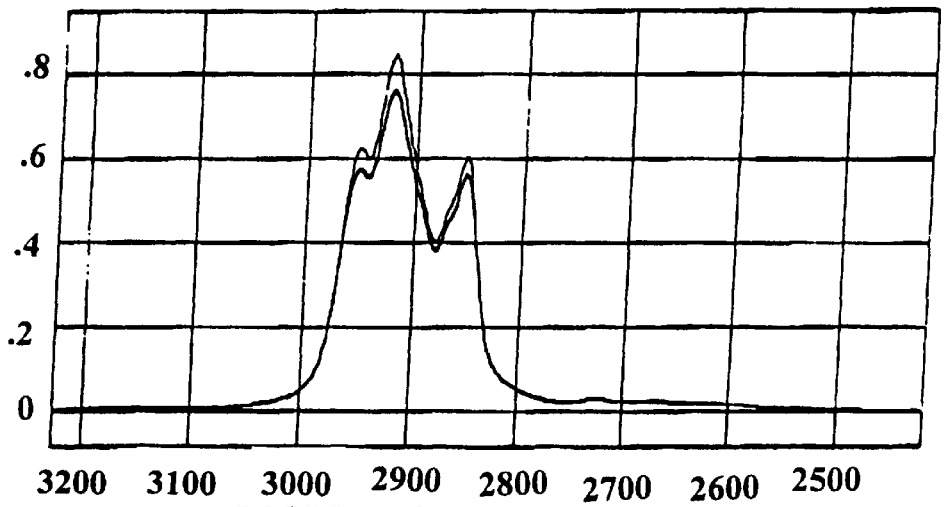
FIG. 4A  ABSORBANCE/WAVENUMBER (cm-1)
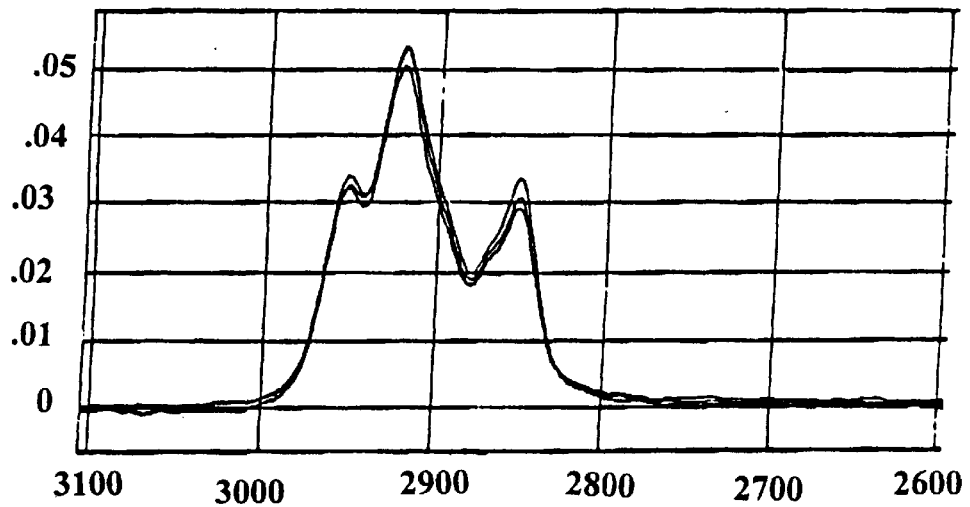
FIG. 4B  ABSORBANCE/WAVENUMBER (cm-1)
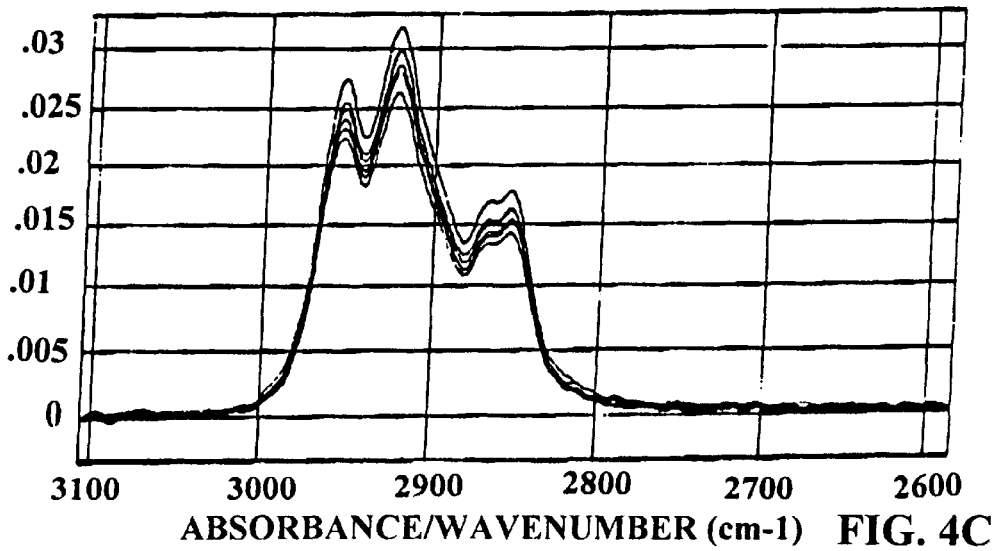
ABSORBANCE/WAVENUMBER (cm-1)  FIG. 4C

SPECTROSCOPIC RESIDUE DETECTION SYSTEM AND METHOD

BACKGROUND OF THE INVENTION

The identification of matter by detecting the spectrum of the electromagnetic radiation reflected from or transmitted through a sample is a well-developed technology. (In this specification and in the claims we use the term, "light" in its broad sense to refer to electromagnetic radiation of any wavelength, including ultraviolet light, visible light and infrared light.) A favorite device for identifying light spectrum is the Michelson interferometer, which was invented by Albert Michelson in 1891 which is still used extensively today. In many modern instruments, based on an improvement invented by Myron Block, the displacement of Michelson's moving mirror is monitored interferometrically along with the detected reflected radiation. Both signals are then analyzed by a computer, which performs a Fourier transform on the collected data to convert a matrix of intensity and displacement data into a spectrum chart of intensity vs wavelength, frequency or wave number. A particular technique, which has been utilized for many years, is the measurement with these spectrometers of diffuse reflectance and diffuse transmittance. When samples of a particular material are illuminated with radiation having a known broad band spectrum, usually in the infrared, visible or ultraviolet range, the sample will absorb and reflect the radiation in a manner that is unique to the particular material.

Integrating spheres have been used for diffuse reflectance spectroscopy since the 1920's. A well-known technique for making diffuse spectrographic measurements involves the use of integrating spheres and a Fourier transform infrared spectrometer. In these devices a necessarily small and rather flat sample is located on a small portion of the inside surface of a sphere having highly reflective diffuse inside surfaces. Infrared light from a broad-band source passes through a slow moving interferometer, illuminates the sample then reflects multiple times from the walls of the integrating sphere and a portion of the light is detected with a detector mounted in a portion of the wall of the sphere. The inside surface of the integrating sphere is rough and very highly reflecting at the wavelength of the illuminating light in order to provide the very large number of diffuse reflections. Systems may utilize a chopped beam so that the detector sees alternating signals from a reference path of source, interferometer, reference, and detector and a sample path of source, interferometer, sample and detector. Special treatments for powder samples and wet samples are usually required before the samples can be analyzed.

FIGS. 1A, 1B and 1C describe a prior art infrared spectrometer, which has been used commercially since the mid-1970's. See Griffiths, *Fourier Transform Infrared Spectrometry*, pages 194–197, published by Wiley-Interscience, New York, N.Y. In this device as shown in FIG. 1A, the displacement of scanning mirror 2 is measured with an HeNe based interferometer system consisting of HeNe laser 6, fixed mirror 4, scanning mirror 2 and laser detector 8. Infrared light beam from source 10 is collimated by mirrors 12 and 14 and split and joined again by beam splitter 16 after the divided beam has reflected off fixed mirror 4 and scanning mirror 2. The recombined beam is reflected off mirror 18 and either passes through chopper 20 or is reflected by it or absorbed by it as chopper 20 rotates. The passing portion, as shown in FIG. 1B, is reflected by mirrors 26 and 28 and illuminates sample 22 in integrating sphere 24. Light not absorbed by the sample is reflected multiple times from the diffusely reflecting inside surface of integrating sphere 24 and a portion of the beam is detected by detector 26. The reflecting portion, as shown in FIG. 1C, is reflected further by mirror 30 and illuminates reference 32. Light not absorbed by reference 32 is reflected multiple times from the diffusely reflecting inside surface of integrating sphere 24 and a portion of the beam is detected by detector 26. When the beam is absorbed by chopper 20, the signal from detector 26 represents a zero energy signal and is subtracted from the sample and reference signals. The signals are analyzed by a computer not shown. The signal from laser detector 8 provides a zero reference twice each time the scanning mirror is displaced by a distance equal to the wavelength of the laser beam. These zero signals are utilized by the computer as a timer to read the infrared signal from detector 26 so that the matrix of collected data is intensity vs mirror displacement. From this array of data the computer calculates the ratio of sample to reference after subtracting the zero signal from each and from the resulting matrix of data, the computer performs a Fourier transform to develop an absorption spectrum for the sample.

The device shown in FIGS. 1A, 1B and 1C and similar devices are very useful in many applications; however, for many other applications a low signal to noise ratio (SNR) has been a problem. Therefore, other diffuse reflectance techniques utilizing optical configurations with better SNR and not involving an integrating sphere have for the most part preempted the systems using integrating spheres. One of these devices uses a paraboloid to focus the beam from the interferometer on to the sample and the light from the sample is collected by another paraboloid and focused onto the detector. This device permits about 15 percent of the light from the interferometer to reach the detector and provides a much better signal to noise ratio.

The prior art of detecting small quantity contaminants, especially from wet processes includes a technique known as attenuated total reflectance (ATR). A solvent containing a contaminant is deposited on IR transparent crystals contained in the trough of a holder and the solvent is allowed to evaporate leaving the contaminant deposited on the transparent crystals. The infrared spectrum is recorded and the data quantified. The ATR technique is deficient in several respects. Errors result if the solution does not completely cover the crystals and when material gets deposited on the walls of the trough. Cleaning the holder, trough and the crystals can be difficult, especially if the crystals are scratched. And the crystals are expensive. Sample preparation can be time consuming. Errors from mishandling samples can result from the many steps required. These problems are usually even more serious in field-testing as co pared to laboratory testing.

What is needed is a better device and method for providing quantitative spectroscopic measurements of very small samples such as low levels of non-volatile contaminants. The need is especially great for field portable and production process measurements.

SUMMARY OF THE INVENTION

The present invention provides a spectroscopic detection system and method. A sample to be analyzed is spread out on the inside surface of a cup portion of a unique detector cup. The cup portion mates with a detector portion of the detector cup to create an enclosed reflecting volume. A small port in the detector portion permits entrance of light which diffusely reflects multiple times from the inside surface of the enclosed reflecting volume and which is partially absorbed by the sample depending on the spectral absorption characteristics of the sample. A light detector in the detector portion detects light after multiple reflections from the surfaces of the detector and cup portions and multiple passes through the sample on the surface of the cup portion. Light detected by the light detector is spectrally analyzed to determine the spectral characteristics of the sample. The invention is useful for detection, identification or quantification, but it is especially valuable for making quantitative measurements of non-volatile residues.

In a preferred embodiment of the present invention the light is infrared light, the diffusely reflecting volume is a sphere, the reflecting surface of the cup is a smooth hemispheric gold surface and the reflecting surface of the detector portion is a rough diffusely reflecting hemispheric gold surface. In this preferred embodiment light from a broad band infrared light source is directed through an interferometer system prior to entering the detector cup and signals from the light detector are Fourier analyzed along with mirror position data to determine absorption characteristics of the sample.

BRIEF DESCRIPTION OF THE DRAWINGS

FIGS. 4A, 4B and 4C are spectroscopic charts showing the repeatability of a preferred embodiment of the present invention.

DETAILED DESCRIPTION OF PREFERRED EMBODIMENTS

Preferred embodiments of the present invention can be described by reference to the drawings.

First Preferred Embodiment

Figure 2:
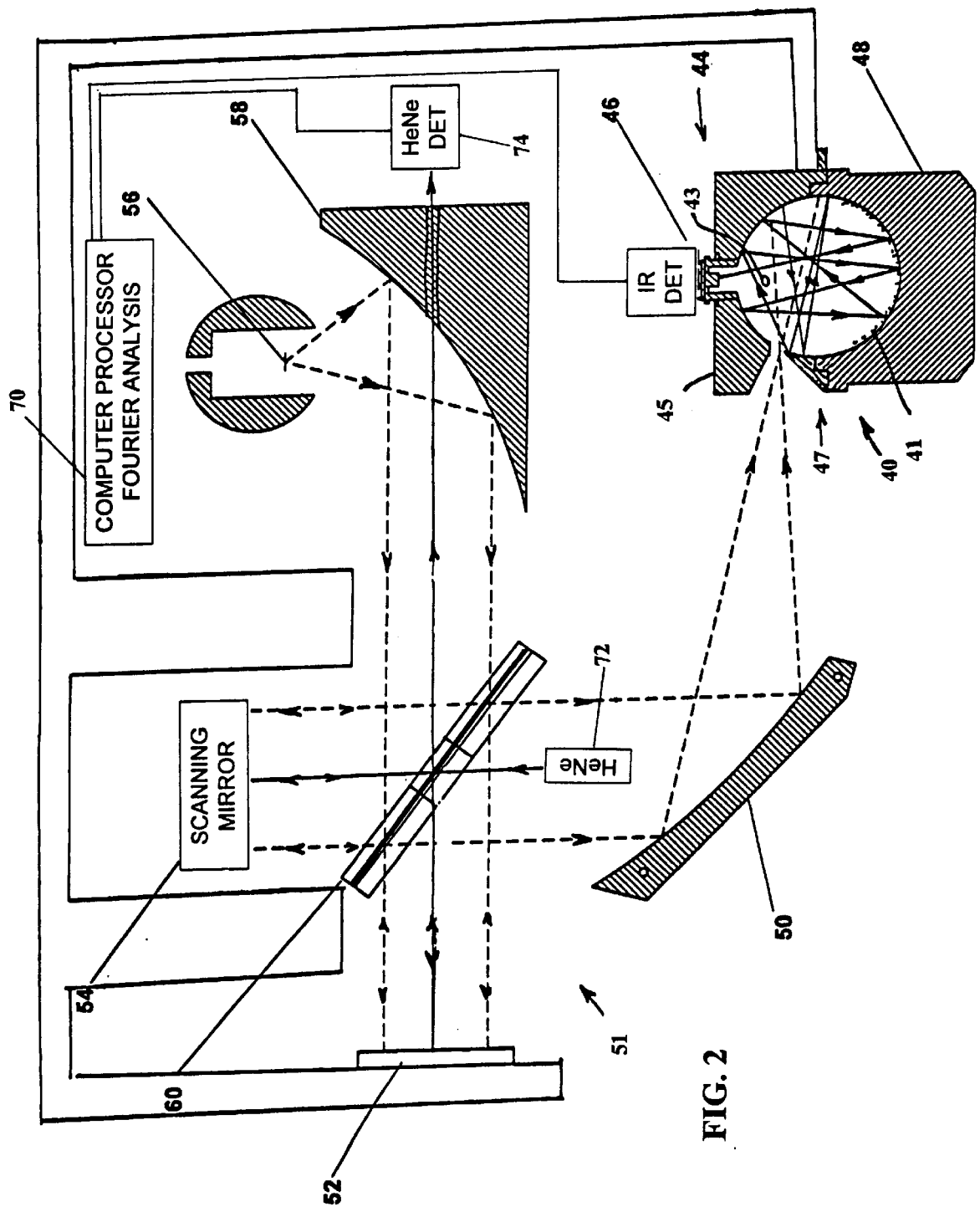
FIG. 2 is a drawing of a preferred embodiment of the present invention utilizing a preferred detector cup in a Fourier transform infrared spectrometer.

A first preferred embodiment of the present invention can be described by reference to FIG. 2. This embodiment is a spectroscopic detection system for quantitative measurements of non-volatile residues. A detector cup 40 is comprised of a detector portion 44 and a cup portion 48. The sample 49 to be measured is spread out on the inside surface of the cup portion. The sample is the residue resulting from the evaporation of a volatile solvent containing a contaminant. The detector portion 44 of the detector cup 40 mates with the cup portion 48 to create an enclosed diffusely reflecting volume with a diameter of 1.125 inches. The detector portion is comprised of structural element 45 and detector 46. The inside surface of structural element 45 of the detector portion 44 is gold plated but roughened to produce a diffusely reflecting surface. A small port (having a diameter on the inside surface of about 0.1-inch and a 30 degree countersink) in the detector portion permits entrance of light from a Michelson interferometer unit 51. Interferometer unit 51 comprises infrared source 56, parabolic mirror 58, beam splitter 60, fixed mirror 52 and scanning mirror 54. Infrared source 56 is in this preferred embodiment a Norton Electronics Model 301 12-volt mini igniter producing black body infrared radiation. Norton Electronics has offices in Milford, N.J. Interferometer 51 also includes a HeNe position detector comprising the same fixed and moving mirrors and also HeNe source 72 and detector 74. The inside surface of cup portion 48 of detector cup 40 is smooth and specular for easy cleaning. (Since the surface is deliberately contaminated in use, reflection tends toward diffuse in most applications.) The light reflects multiple times from the inside surface of the enclosed reflecting volume and is partially absorbed by sample 49 depending on the spectral absorption characteristics of sample 49. A light detector 46 detects light after multiple reflections from the surface of the detector and cup portions of detector cup 44 and multiple passes through and reflections from sample 49 on the surface of the cup portion 48. Light detector 46 is in this embodiment is a pyro-electric detector, Model No. P99/5121, (available from McGee Components, Inc., North Attleboro Mass., 02760). The reflecting surface of the detector portion is rough and highly diffusely reflective. A parabolic mirror 50 focuses light through small port 51 into detector cup 40. The arrowed lines inside detector cup 40 illustrate the path of a typical photon as it reflects many times from the gold surface of detector cup 40 and passes multiple times through sample 49. (The photon whose path is depicted is one whose wavelength is not within a high absorption spectral range of the sample and as shown is not absorbed and ultimately is detected by detector 46.) Spectral data is recorded by computer processor 70 from signals provided by detector 46 at intervals determined using a HeNe interferometer system comprising HeNe laser 72 and HeNe detector 74 so as to obtain a matrix of intensity data at constant very small displacement intervals. The matrix of data is analyzed by computer processor 70 using a fast Fourier transform in order to determine the spectral characteristics of the sample. Preferably the computer is programmed to provide the spectral information in graphical form such as the graphs shown in FIGS. 3 through 7.

A specific preferred embodiment has been built and tested by Applicants. For this embodiment Applicants modified a commercially available spectrometer, Model SOC 400 Surface Inspection Machine/Infrared, available from Surface Optics Corporation with offices in San Diego, Calif. The modification includes the addition of parabolic mirror 50 and the replacement of an existing detector with the detector portion of detector cup 40. The detector portion 44 is permanently attached to the spectrometer and becomes an integral part of it. Detector portion 44 comprises small purge port 43 to which a nitrogen purge line is attached for purging the detector cup with a very low flow of nitrogen. The cup portion 48 attached to the detector portion with screw threads at 45 and is detachable merely by screwing it off. In this embodiment the inside surface of detector portion 44 of detector cup 40 is a sand blasted gold plated surface to create a very highly diffusely reflecting surface. The inside surface of cup portion 48 of detector cup 40 is gold plated and smooth to provide a very highly reflecting specular surface which is easy to clean and reuse.

Quantitative Analysis of Contaminants

The development of the above-described embodiment of the present invention was in response to a need to analyze small amounts of dissolved contaminants in a volatile solvent. The dissolved contaminant is introduced into the solvent when a contaminated part is rinsed with the solvent. The solvent is collected and analyzed for the presence of contaminants. Repeated washings are required until the contamination is reduced to an acceptable level. The prior art method of analysis utilized an ATR-FTIR system discussed in the Background section. The above embodiment greatly simplifies the analyses of contamination in volatile solvents producing more accurate and more repeatable results.

Low Detection Levels

Figure 1A:
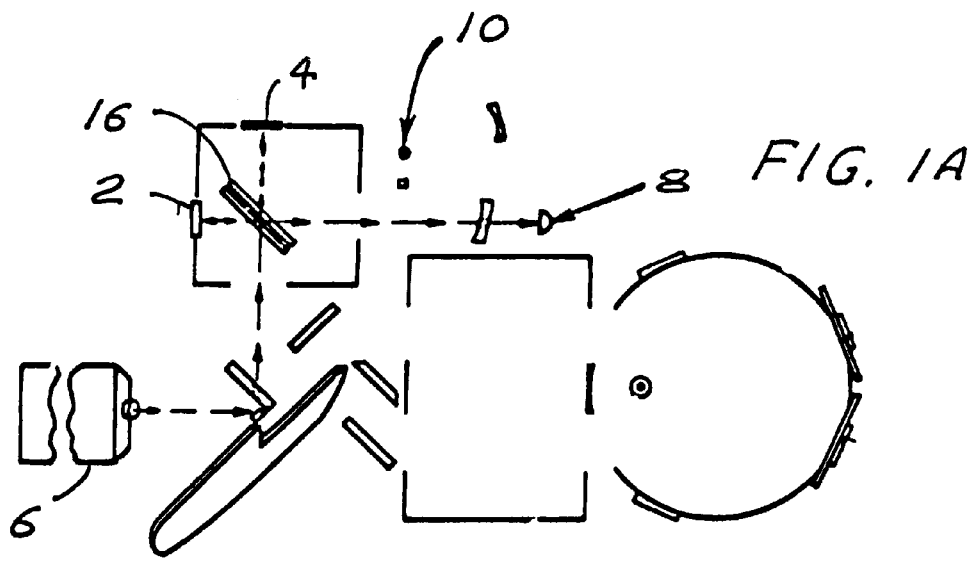
FIGS. 1A, 1B and 1C are drawings of a prior art spectroscopic device utilizing an integrating sphere.

The detector cup owes its ability to measure very small amounts of contaminants to the fact that the detected IR light bounces around inside the cavity and passes through the sample material many times before it is detected. Photons are given many opportunities to be absorbed by any contaminant deposited on the inside surface of cup portion 48. The result is the detector cup permits very low detection levels. In the device shown in FIGS. 1A, B and C most photons pass through the sample site only once.

Repeatability

Methods utilizing the detector cup have shown excellent repeatability. Applicants have experimented with low contamination level samples by filling cup 48 halfway, all the way, tilted on its side or with just a small drop on the bottom. The results show that the results are the same depending only on the quantity of contaminant. Applicants believe that this excellent repeatability is a consequence of the integrating nature of the detector cup. Therefore, the result is the same whether the contaminant is evenly distributed over the entire surface of the cup portion or concentrated on a smaller section of the surface.

Comparison with Prior Art Integrating Sphere

Figure 1B:
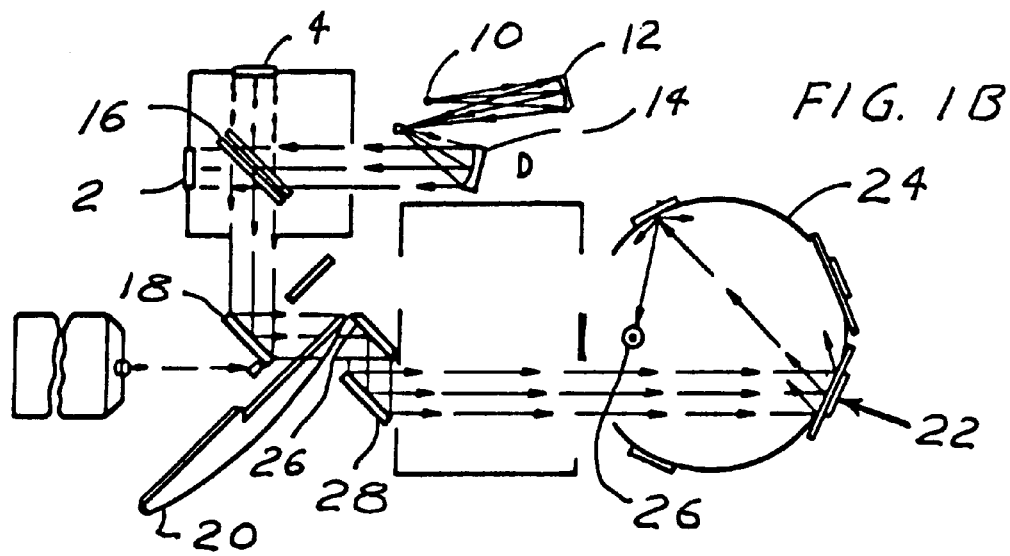
Figure 1C:
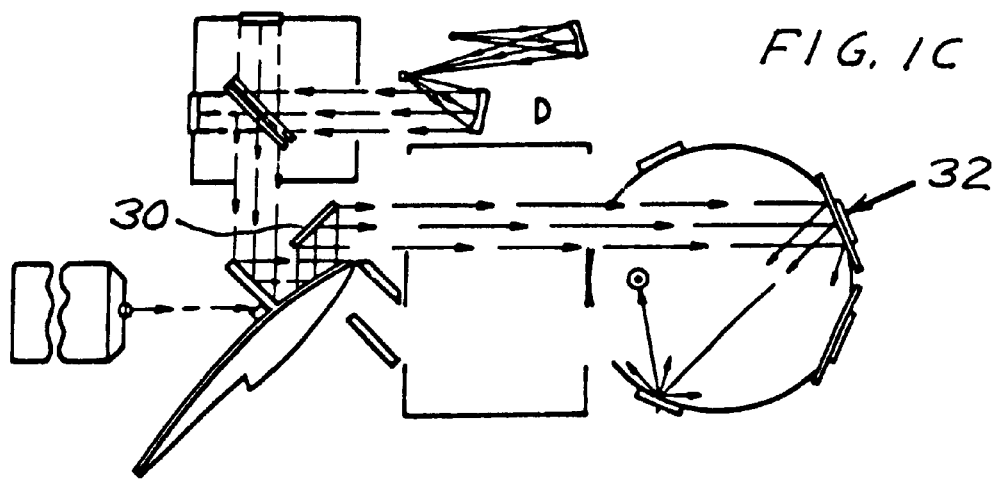

As indicated in the Background section, integrating spheres have been around for a long time. The important differences between the present invention and the prior art integrating spheres are discussed below. The prior-art integrating sphere has a small sample port, which contains the sample and is illuminated directly by the beam from the source, but only a very small portion of the reflected light illuminates the sample. The detector cup of the present invention comprises a cup portion having an inside surface over which the sample may be distributed. Contaminating the inside surface of the prior art integrating sphere destroys the setup for analysis and could destroy the usefulness of the sphere unless it could be cleaned, which typically would be very difficult because the surface was rough for diffuse reflections. The cup portion of the detector cup of the present invention is made to be cleaned between uses and the cleaning job is easy because of the smooth surface. Use of the prior art integrating sphere required the depositing of the sample at the sample port in a condition for analysis. Use of the present detector permits a volatile solvent containing a contaminant to be placed in the cup after which the solvent is evaporated. This greatly simplifies the analysis process in many applications, particularly the type of analysis discussed above where the contaminant is already in the solvent. It is important for the reader to appreciate the levels of detection for the present invention are about 10 to 100 times lower that those of a system such as that described in FIG. 1.

Other Analysis Techniques

A preferred technique is to swab a test area, such as one square foot of the surface of a component suspected of being contaminated, with a cotton swab. Thereafter dissolve any hydrocarbon contaminant on the swab in cyclohexane. The solution is then deposited in cup portion 48 of detector cup 40 and the cyclohexane is allowed to evaporate leaving any hydrocarbon contaminate deposited on the smooth gold inside surface of cup portion 48 as shown at 41 in FIG. 2. The absorption spectrum of the sample is then determined as described above.

Persons skilled in the art of spectroscopic analysis will understand that there are very many other available techniques for depositing the sample in the cup portion of detector cup 48, for example, smearing on to the surface simi-volatile liquids such as diesel fuel or a non-volatile liquid such as mineral oil. Another interesting technique involves the cooling of a gas to its liquid or solid phase and causing it to deposit on the walls of a cooled cup.

Experimental Results

Figure 3:
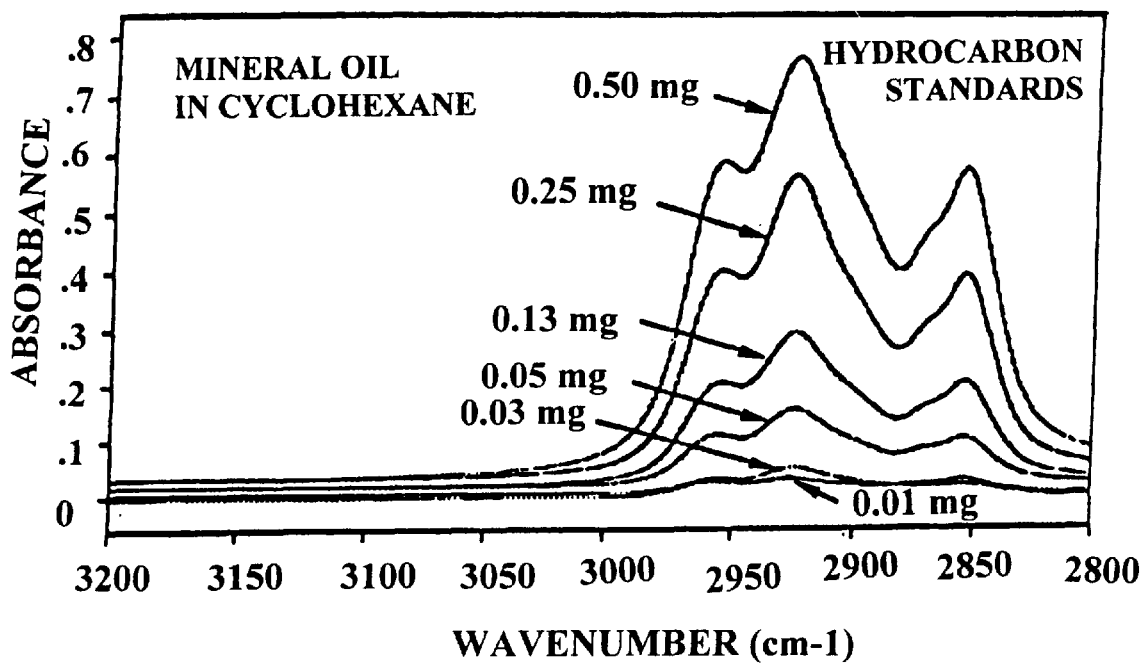
FIG. 3 is a chart showing spectroscopic calibration curves made for an embodiment of the present invention.

Experiments have been performed to evaluate the accuracy of this embodiment. The first sets of test data are described below. Standard solutions of mineral oil were prepared in cyclohexane. A calibration curve was obtained from 0.01 mg to 0.50 mg on the SOC-400 Fourier transform infrared spectrometer as shown in FIG. 3. An infrared absorption spectrum was obtained between 3000 $cm^{-1}$ and 2800 $cm^{-1}$ wavenumbers. Sixty-four scans at 8 $cm^{-1}$ resolution were obtained.

Results of preliminary testing are summarized in Table I. The recoveries and repeatability are very good with the exception of the lowest concentrations.

TABLE I

| Amount In Sample (mg) | Amount Detected (mg) |
|---|---|
| 0.01 | 0.02 |
| 0.01 | 0.02 |
| 0.01 | 0.02 |
| 0.01 | 0.02 |
| 0.03 | 0.03 |
| 0.03 | 0.02 |
| 0.05 | 0.05 |
| 0.13 | 0.11 |
| 0.13 | 0.10 |
| 0.25 | 0.27 |
| 0.50 | 0.49 |
| 0.02 | 0.03 |
| 0.25 | 0.23 |
| 0.50 | 0.40 |

These preliminary test results have shown that the present invention provides excellent quantitative results and that accuracies in the range of about 0.01 mg to 0.02 mg are possible. Subsequent testing shows that the repeatability of the measurements is excellent. FIGS. 4A, 4B and 4C show the results respectively of four repeated tests on the same quantity of 0.5 mg, three repeated tests with 0.25 mg and seven tests repeated with 0.1 mg. In each case 64 scans were made with the interferometer set for an 8 $cm^{-1}$ resolution.

Advantages of the Detector Cup

As indicated in the Background section the current practice of analyzing for small quantities of contaminants in a solvent utilizes an ATR technique of depositing the contaminated solvent in a trough containing a transparent crystal. This technique has proven much more stable than techniques such as the older integrating sphere techniques. The above-described embodiment of the present invention constitutes an important improvement in the process of analyzing for small quantities of contaminants dissolved in a solvent. All the nonvolatile material deposited in the cup portion is measured. Quantities of hydrocarbons of less than 10 micrograms (0.000000352 ounce) can be measured. Small or large volumes (up to about 5 milliliters) of contaminated solvent can be simply deposited and evaporated in the cup portion. The detector cup is easily cleaned. The cup portion is rugged, inexpensive to produce so that many cups can be provided at low cost. Sample preparation is simple and easy. The present invention may permit elimination of a pre-concentration step, which would have been required with prior art techniques. In some situations (such as when only detection is sought) evaporation may not be necessary. The technician could just pour contaminated liquid into the cup, swish it around, pour the liquid out and measure what remains on the inside surface of the cup portion of the detector cup. This simplified procedure could be used for intermediate checks during a several-step cleaning process.

Other Detector Cup Shapes

Figure 5A:
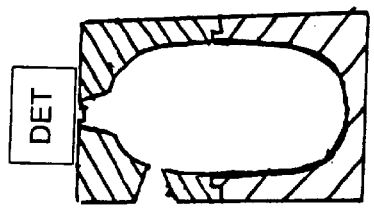
FIGS. 5A, 5B and 5C show some alternate detector cavity shapes.
Figure 5B:
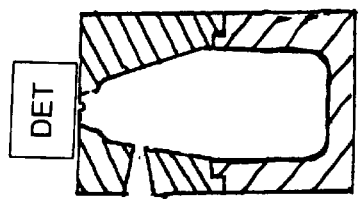
Figure 5C:
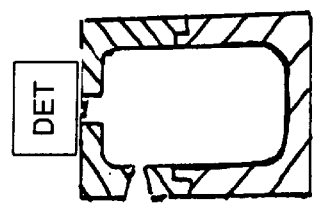

Persons skilled in the optics art should recognize that shapes other than spherical could be used for the detector cup. What are required are a large surface area and a large number of randomized reflections. Preferred cavity shapes may vary with factors such as wavelengths, material handling requirements and with manufacturing processes when this invention is incorporated into the manufacturing process. Other preferred cavities include cylindrical, conical and oval as shown in FIGS. 5A, 5B and 5C. In each case, preferably the inside surface of detector portion is diffusely reflecting and the inside surface of cup portion is smooth for ease of cleaning as in the above-described preferred embodiment. The inside surface materials should be chosen taking into consideration the type of light that is intended for use with the detector cup.

Other Spectrometer Techniques

Figure 6:
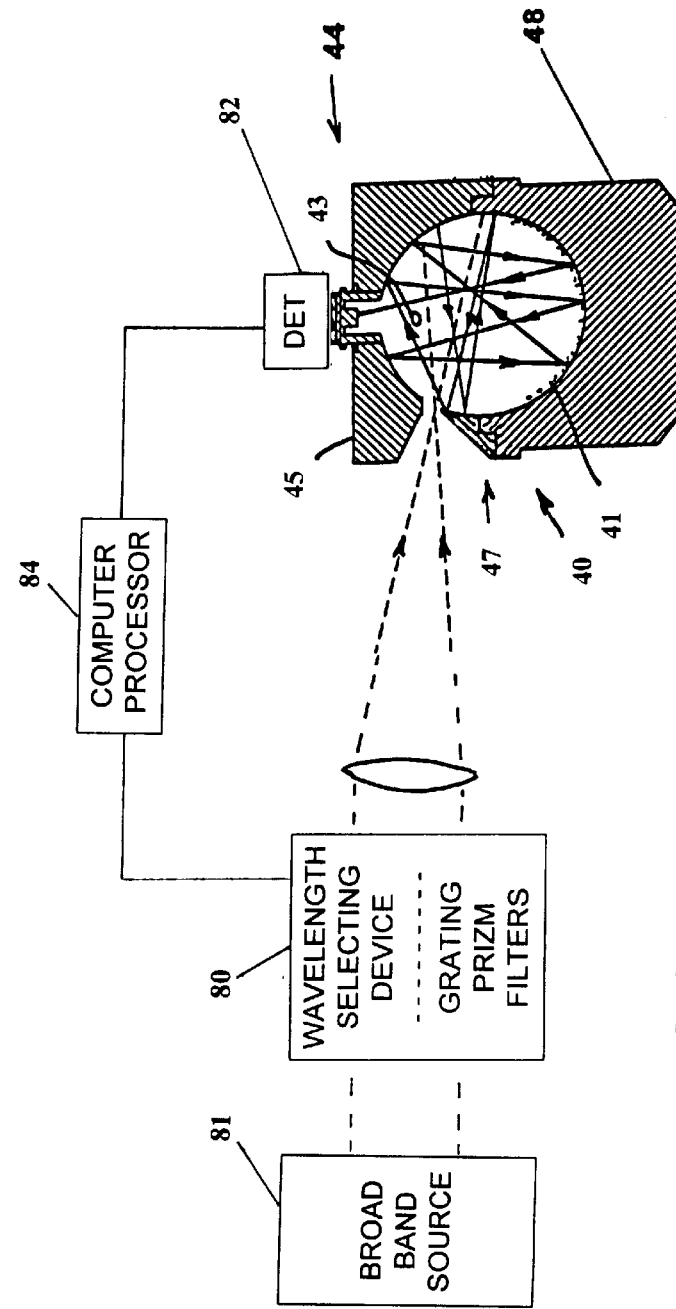
FIG. 6 is a sketch showing the detector cup in a spectrometer comprising a wavelength-selecting element.
Figure 7:
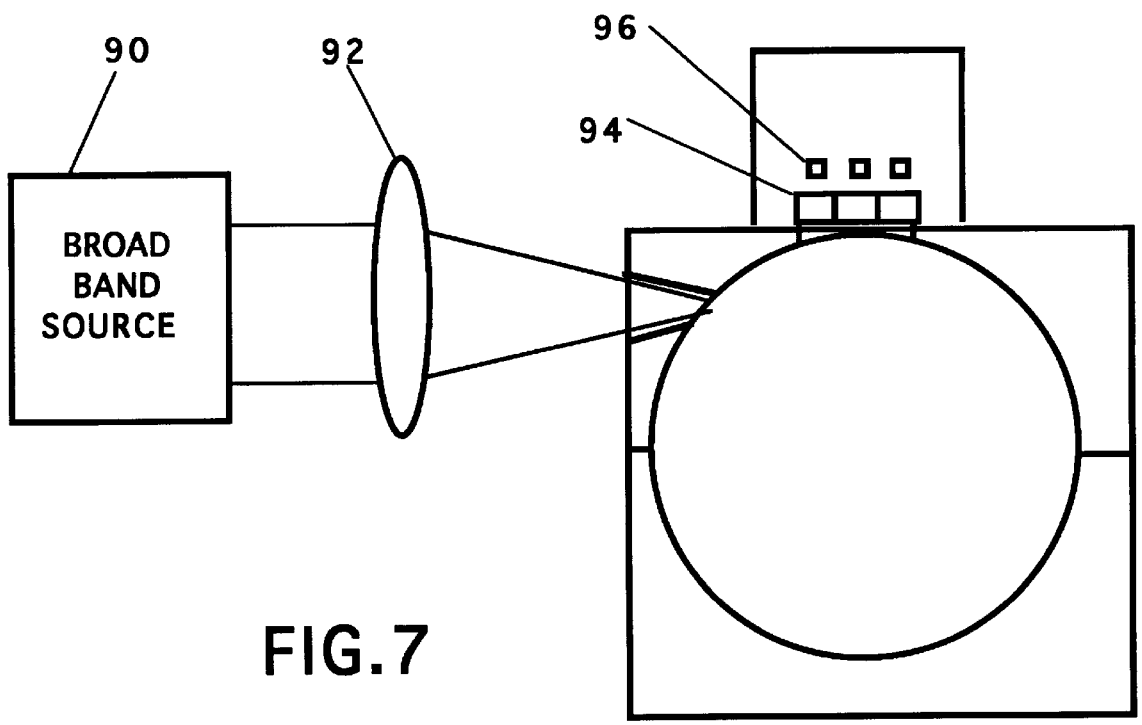
FIG. 7 is a sketch of an embodiment in which spectral separation and detection are both down stream of the enclosed reflecting volume.

The embodiment described in detail above utilizes the detector with other elements of an FTIR spectrometer. Persons skilled in the spectrometer art will readily recognize that the detector cup of the present invention can be used in many other spectroscopic instruments. These other spectrometer possibilities include grating-based spectrometers, prism-based spectrometers, and filter-based spectrometers including circular variable filters and similar instruments. In these other cases, a wavelength-selecting device 80 (such as the grating, prism or filter device) selects light from a broad band source 81 at particular wavelengths that illuminate the inside surfaces of the detector cup 40 as indicated in FIG. 6. A detector 82 sensitive to the selected wavelengths detects the intensity of the light after multiple reflections inside the detector cup and absorption by the sample material deposited on the inside surface of the cup portion of the detector cup and the results are analyzed by computer 84. Spectral separation can be upstream or downstream of the enclosed reflecting volume. A downstream example is shown in FIG. 7. There a broad band source 90 is focused by lens 92 to illuminate the enclosed reflecting volume. A 3×3-filter array of 9 filters 94 and a 3×3-detector array 96 are used to analyze the light from the reflecting volume. Filter-detector arrays as shown in FIG. 7 are commercially available from suppliers such Cal-Sensors, Inc. with offices in Santa Rosa, Calif.

While the above embodiments have been described with specificity, persons skilled will recognize that many changes and modifications could be made to both the equipment and processes described without departing from the basic concepts disclosed. For example, it should be clear that the detector cup could be utilized with many commercially available spectrometers. In many situations a large variety of cup designs for the cup portion could be made available with various cavity geometries, surfaces and substrates. These cup assemblies could be provided as a set. Also, a variety of detector cups (including detector portions and cup portions) could also be provided. These could be made modular so that the detector portion could be relatively easily replaced, so that the entire detector cup could be changed out for different measurements. Therefore, the scope of the inventions is to be determined by the appended claims and their legal equivalents.

We claim:

1. A residue detection system for spectroscopic analysis of non-volatile residues comprising:
    A) a light source,
    B) a detector cup comprising:
        1) a detector portion comprising:
            a) a light detector,
            b) a structural element defining a detector portion inside surface and
            c) a light port, and
        2) a cup portion defining a cup portion inside surface, said cup portion inside surface defining a cup portion inside surface area, and containing a sample spread over at least half of said inside surface area, said cup portion being releasably attached to said detector portion such that said detector portion and said cup portion inside surfaces define an enclosed diffusely reflecting volume,
    C) an optical train for directing light from said light source into said enclosed diffusely reflecting volume,
    D) a processor for analyzing signals produced by said light detector to determine optical characteristics of said sample;

wherein said light detector in said detector portion detects light from said light source after multiple reflections from the surfaces of the detector and cup portions and multiple passes through the sample deposited on said cup portion inside surface.

2. A system as in claim 1 wherein said optical train comprises a fixed mirror and a moving mirror and a means for measuring positions of said moving mirror.

3. A system as in claim 2 wherein said processor is programmed to collect a intensity data from said light detector and moving mirror position data and to determine light spectra based on a matrix of said intensity data and said position data.

4. A system as in claim 3 wherein said light source comprises an infrared light source, said processor is programmed to perform Fourier transform analyses and said system defines a Fourier transform infrared spectrometer.

5. A system as in claim 1 wherein at least a large portion of said detector portion inside surface is diffusely reflecting and said cup portion inside surface is a smooth spectrally reflecting surface.

6. A system as in claim 1 wherein said detector portion also comprises a purge port.

7. A system as in claim 1 wherein said enclosed diffusely reflecting volume is substantially spherical.

8. A system as in claim 1 wherein said enclosed diffusely reflecting volume is substantially cylindrical.

9. A system as in claim 1 wherein said enclosed diffusely reflecting volume is partially conically shaped.

10. A system as in claim 1 wherein said enclosed diffusely reflecting volume is substantially oval.

11. A system as in claim 1 wherein said optical train comprises a wavelength-selecting element.

12. A system as in claim 11 wherein said wavelength selecting element is selected from a group consisting of gratings, prisms and optical filters.

13. A system as in claim 11 wherein said wavelength selecting element is upstream of said enclosed diffusely reflecting volume.

14. A system as in claim 11 wherein said wavelength selecting element is downstream of said enclosed diffusely reflecting volume.

15. A method of performing spectroscopic analysis utilizing a spectroscopic residue detection system for analysis of non-volatile residues comprising:
   A) a light source,
   B) a detector cup comprising:
      1) a detector portion comprising:
         a) a light detector,
         b) a structural element defining a detector portion inside surface and
         c) a light port, and
      2) a cup portion defining a cup portion inside surface, said cup portion inside surface defining a cup portion inside surface area, said cup portion being releasably attachable to said detector portion such that when attached said detector portion and said cup portion inside surfaces define an enclosed diffusely reflecting volume,
   C) an optical train for directing light from said light source into said enclosed diffusely reflecting volume,
   D) a processor for analyzing signals produced by said light detector to determine optical characteristics of said sample;
   said method comprising the steps of:
      A) dissolving at least one contaminant in a volatile solvent,
      B) depositing said contaminant containing solvent in said cup portion,
      C) evaporating said volatile solvent to leave a sample of residue deposited on an area constituting at least half of the cup portion inside surface area,
      D) attach said cup portion to said detector portion,
      E) directing light into said detector cup,
      F) processing signals from said detector to determine optical characteristics of said sample;
   wherein said light detector in said detector portion detects light from said light source after multiple reflections from the surfaces of the detector and cup portions and multiple passes through the sample deposited on said cup portion inside surface.

16. A method as in claim 15 wherein said optical train comprises a fixed mirror and a moving mirror and a means for measuring positions of said moving mirror.

17. A method as in claim 16 wherein said processor is programmed to collect a intensity data from said light detector and moving mirror position data and to determine light spectra based on a matrix of said intensity data and said position data.

18. A method as in claim 17 wherein said light source comprises an infrared light source, said processor is programmed to perform Fourier transform analyses and said system defines a Fourier transform infrared spectrometer.

19. A method as in claim 15 wherein at least a large portion of said detector portion inside surface is diffusely reflecting and said cup portion inside surface is a smooth spectrally reflecting surface.

20. A method as in claim 15 wherein said detector portion also comprises a purge port.

21. A method as in claim 15 wherein said enclosed diffusely reflecting volume is substantially spherical.

22. A method as in claim 15 wherein said enclosed diffusely reflecting volume is substantially cylindrical.

23. A method as in claim 15 wherein said enclosed diffusely reflecting volume is partially conically shaped.

24. A method as in claim 15 wherein said enclosed diffusely reflecting volume is substantially oval.

25. A method as in claim 15 wherein said optical train comprises a wavelength-selecting element.

26. A method as in claim 25 wherein said wavelength selecting element is selected from a group consisting of gratings, prism and optical filters.

27. A method of performing spectroscopic analysis utilizing a spectroscopic residue detection system for analysis of non-volatile residues comprising:
   A) a light source,
   B) a detector cup comprising:
      1) a detector portion comprising:
         a) a light detector,
         b) a structural element defining a detector portion inside surface and
         c) a light port, and
      2) a cup portion defining a cup portion inside surface, said cup portion inside surface defining a cup portion inside surface area, said cup portion being releasably attachable to said detector portion such that when attached said detector portion and said cup portion inside surfaces define an enclosed diffusely reflecting volume,
   C) an optical train for directing light from said light source into said enclosed diffusely reflecting volume,
   D) a processor for analyzing signals produced by said light detector to determine optical characteristics of said sample;
   said method comprising the steps of:
      A) dissolving at least one contaminant in a solvent to make a contaminated solvent,
      B) depositing said contaminated solvent in said cup portion,
      C) swishing said contaminated solvent in said cup then pouring out of said cup portion substantially all of said contaminated solvent to leave a sample of residue deposited on at least half of said cup portion inside surface area,
      D) attach said cup portion to said detector portion,
      E) directing light into said detector cup,
      F) processing signals from said detector to determine optical characteristics of said sample of residue;
   wherein said light detector in said detector portion detects light from said light source after multiple reflections from the surfaces of the detector and cup portions and multiple passes through the sample deposited on said cup portion inside surface.

* * * * *